United States Patent [19]

Hermkens et al.

[11] Patent Number: 5,106,840
[45] Date of Patent: Apr. 21, 1992

[54] METHOD OF PREPARING N-OXO-TETRAHYDRO-BETA-CARBOLINES

[75] Inventors: Peter H. H. Hermkens; Jan H. Van Maarseveen; Johan W. Scheeren; Cornelis G. Kruse, all of Weesp, Netherlands

[73] Assignee: Duphar International Research B.V., Weesp, Netherlands

[21] Appl. No.: 533,415

[22] Filed: Jun. 5, 1990

[30] Foreign Application Priority Data

Jun. 8, 1989 [NL] Netherlands ............... 8901458

[51] Int. Cl.$^5$ .............. A61K 31/39; C07D 515/14
[52] U.S. Cl. .............................. 514/183; 514/211; 514/222.8; 514/229.2; 514/229.5; 540/468; 540/496; 540/545; 540/546; 544/2; 544/63; 544/66
[58] Field of Search ............ 540/468, 496, 545, 546; 544/66, 63, 2; 514/183, 211, 222.8, 229.2, 229.5

[56] References Cited

U.S. PATENT DOCUMENTS 4,631,149 12/1986 Rinehart et al. ................. 540/546

OTHER PUBLICATIONS

J. Am. Chem. Soc. 109, 3378, (1987), and Tetrahedron Letters, 29, 2255 (1988).
Tetrahedron Letters 28, 4971 (1988), and Austr. J. Chem 42, 1201 (1989).
Tetrahedron Letters, 30, 1041, (1989), and J. Am. Chem. Soc. 11, 2721 (1989).
J. Org. Chem., 47, 2147 (1982), and J. Chem. Soc. (1965) 7179.
J. Chem. Soc., Chem. Comm. 1979 514.
J. Chem. Soc. Comm. 1979, 495, and J. Org. Chem. 44, 1247 (1979).

Primary Examiner—Robert T. Bond
Attorney, Agent, or Firm—Stevens, Davis, Miller & Mosher

[57] ABSTRACT

The invention relates to a method of preparing N-oxo-tetrahydro-β-carbolines having formula 1.

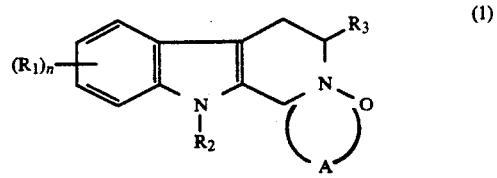

wherein
$R_1$ is lower alkyl or alkoxy, halogen, trifluoromethyl, lower alkylthio, hydroxy, amino, lower mono- or dialkyl- or acylamino.
n has the value 0, 1 or 2,
$R_2$ is hydrogen, lower alkyl or acyl,
$R_3$ is hydrogen, lower alkyl or alkoxycarbonyl, or a phenyl group optionally substituted with a group $R_1$, and
A together with the group —C—N—O—, forms a saturated heterocyclic ring systems consisting of 6-8 ring atoms, wherein, in addition to the already present oxygen atom and nitrogen atom, an extra hetero atom from the group, O, S and N may be present, which ring system may be substituted with one or more of the substituents alkyl, alkoxycarbonyl, alkanoyl, alkoxy, hydroxy, oxo, amino, mono- or dialkylamino, alkanoyl-or alkoxycarbonylamino, which ring system may be annelated with a saturated carbocyclic group of 5 or 6 ring atoms, by an intramolecular ring closure reaction of compounds of formula 2

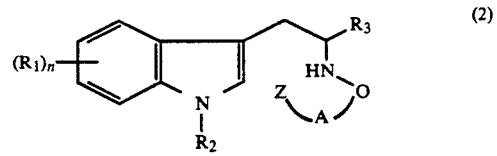

wherein Z is an aldehyde function or acetal function, or is a functional group which can be converted into such a funciton during the ring closure reaction.

The eudistomin derivatives within the group of compounds having formula 1 have strong antiviral and antitumor activity.

15 Claims, No Drawings

METHOD OF PREPARING N-OXO-TETRAHYDRO-BETA-CARBOLINES

The invention relates to a new method of preparing known and new N-oxo-tetrahydro-β-carbolines.

It is known that some alkaloids of the tetrahydro-β-carboline type, for example, yohimbine, vincamine and corynantheine, have interesting pharmacological properties (ref. 1).

Furthermore, it was recently described that a few tetrahydro-N-oxocarboline compounds (the so-called eudistamins) show a strong antiviral activity with respect to Simplex- and polio virus (ref. 2); in addition they have an antitumour activity (ref. 3). These eudistamins have been isolated in very small quantities from biological material (ref. 2) and have been obtained via a total synthesis in a very low yield (ref. 4).

It has now been found that compounds of formula 1

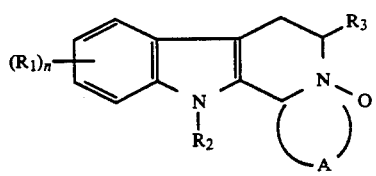

wherein
- R₁ is lower alkyl or alkoxy, halogen, trifluoromethyl, lower alkylthio, hydroxy, amino, lower mono- or dialkyl-or acylamino,
- n has the value 0, 1 or 2,
- R₂ is hydrogen, lower alkyl or acyl,
- R₃ is hydrogen, lower alkyl or alkoxycarbonyl, or a phenyl group optionally substituted with a group R₁, and
- A together with the group —C—N—O—, forms a saturated heterocyclic ring system consisting of 6-8 ring atoms, wherein, in addition to the already present oxygen atom and nitrogen atom, an extra hetero atom from the group O, S and N may be present, which ring system may be substituted with one or more of the substituents alkyl, alkoxycarbonyl, alkanoyl, alkoxy, hydroxy, oxo, amino, mono- or dialkylamino, alkanoyl- or alkoxycarbonylamino, which ring system may be annelated with a saturated carbocyclic group of 5 or 6 ring atoms, can be obtained in a good yield by an intramolecular ringclosure reaction of compounds of formula 2

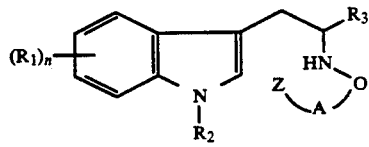

wherein R₁, n, R₂, R₃ and A have the meanings given hereinbefore, and Z is an aldehyde function or an acetal function, or is a functional group which can be converted into such a function during the ring closure reaction.

In the meanings defined hereinbefore of the symbols used, groups having 1-4 C-atoms are denoted by alkyl or alkoxy, alkylthio, lower alkyl, alkoxy or alkylthio.

Group Z in the starting compounds of formula 2 for the intramolecular cyclisation reaction according to the invention is a group which is capable of performing a double electrophilic attack on both the aliphatic nitrogen atom and the carbon atom of the indole ring. On the one hand it relates notably to aldehyde groups and acetal groups and on the other hand to ester groups. In the former case the so-called Pictet-Spengler cyclisation occurs under the influence of an acid catalyst, for example, trifluoroacetic acid. In the other case a reductor, for example, diisobutyl aluminum hydride (DIBAL) is also used to generate the required level of oxidation at the C-atom of the group Z.

The starting compounds of formula 2 can be obtained by reaction of a compound of formula 3

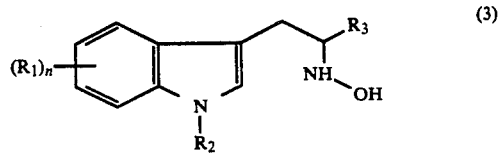

with a compound of formula 4

in which formulae R₁, n, R₂, R₃, A and Z have the above-mentioned meanings, and X is a so-called leaving group, preferably halogen or a sulphonate group.

Compounds of formula 3 are partly known compounds (ref. 5) or can be obtained analogously to the known compounds.

The compounds of formula 4 can be obtained in a manner known for the preparation of this type of compounds.

The coupling of a compound of formula 3 with a compound of formula 4 cannot be carried out as such because the hydroxyamino group in formula 3 would react non-selectively with the compound of formula 4, since both the nitrogen atom and the oxygen atom have nucleophilic properties. It has been found that in the reaction of a compound of formula 3 with compound of formula 4 the coupling takes place exclusively on the oxygen atom when first the nitrogen atom is protected selectively. After the coupling reaction and removal of the protecting group from the nitrogen atom, the desired compound of formula 2 is obtained.

Examples of good protecting groups for the nitrogen atom are acyl or alkoxycarbonyl, for example, trichloroethoxycarbonyl or 2-(trimethylsilyl) ethoxycarbonyl. The protecting group may be removed in a manner known per se, for example, as described in (ref. 6).

When a functional group which should be protected during the synthesis route described hereinbefore, for example, hydroxyl groups or amino groups, is present in one or more of the groups R₁, R₂, R₃ or A, these protecting group(s) may be removed again in a manner known per se after the synthesis, after which the endeavoured compound of formula 1 is obtained.

The compounds of formula 1 are new compounds with the exception of a number of eudistamin derivatives of formula 5

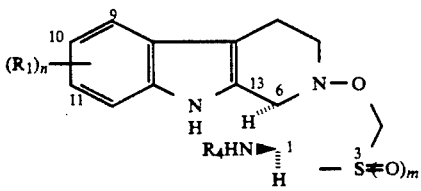

wherein
- a) m and n are 0, and $R_4$ is hydrogen or tert.butoxycarbonyl (Boc), or
- b) n is 1, m is 0 or 1, $R_1$ is 11—Br and $R_4$ is hydrogen or acetyl, or
- c) n is 1, m is 0, $R_1$ is 10—Br and $R_4$ is hydrogen or Boc, or
- d) n is 2, m is 0, $R_1$ is 10—OH, 11—Br, and $R_4$ is hydrogen, or
- e) n is 2, m is 0, $R_1$ is 9—Br, 10—OH, and $R_4$ is hydrogen, on the understanding that the stereochemical configuration both at $C_1$ and $C_{13b}$ is the S-configuration, and that the optionally oxide substituent at $S_3$ is in the cis position in view of the substituent at $C_1$.

The process according to the invention is particularly suitable for the stereo-selective total synthesis of both new and known eudistamin derivatives. The processes used so far (ref. 4) are characterised by an inversion of the sequence in which the functional groups in compounds of the formulae 3 and 4 are coupled to each other. However, this results in complete racemisation at carbon atom C-1 in the first reaction step (i.e. an intermolecular Pictet-Spengler reaction), and/or gives extremely low yields in the second step (i.e. formation of a thermodynamically unfavourable 7-membered ring). These disadvantages do not occur when the above described new method is used.

A further aspect of the invention is a new method for the preparation of eudistamins wherein $R_4$ is hydrogen starting with the corresponding compound wherein $R_4$ is Boc. The known method (ref. 4) with a strong acid (trifluoroacetic acid, TFA) is very inefficient and results in extensive degradation of the desired product. It has surprisingly been found now that treatment of the compound containing the Boc-group with another electrophilic reagent (trimethylsilyl halide, see ref. 7) gives the desired compounds in very good yields.

The invention also relates to the new compounds of formula 1 and the salts thereof. When one or more chiral centres are present, the invention relates to the various diastereo isomers and enantiomers, and to (racemic) mixtures thereof.

Compounds having formula 1 have interesting farmacological properties. Similar to some known eudistomins also the new compounds having formula 5 have strong antiviral and antitumour activity. It has surprisingly been found that compounds nos. 63 and 67 have a very broad spectrum of antiviral activity in 22 antiviral test models. This is unique in comparison with known antiviral agents, such as for example acyclofur, ribavirin and other nucleoside analogs. Moreover, new compound no. 67 has been found to have at least ten times higher potency in comparison with known compound 63, which is found in nature.

The compounds of formula 1 and suitable salts thereof may be brought into forms suitable for administration, for example, pills, tablets, coated tablets, capsules, powders, injection liquids and the like while using techniques and auxiliary substances conventionally used for this purpose.

The invention will now be described in greater detail with reference to the following specific examples.

The references referred to hereinbefore are:
ref. 1: J. E. Saxton (editor) in "The chemistry of heterocyclic compounds", vol. 25, part 4 (1983).
ref. 2: J. Am. Chem Soc. 109, 3378, (1987), and Tetrahedron Letters, 29, 2255, (1988).
ref. 3: Tetrahedron Letters 29, 4971 (1988), and Austr. J. Chem 42, 1201 (1989)
ref. 4: Tetrahedron Letters, 30, 1041, (1989) and J. Am. Chem. Soc. 111, 2721 (1989).
ref. 5: J. Org. Chem. 47, 2147 (1982), and J. Chem. Soc. (1965), 7179.
ref. 6: J. Chem. Soc. Chem. Comm. 1979, 514
ref. 7: J. Chem. Soc. Comm. 1979, 495, and J. Org. Chem. 44, 1247 (1979).
ref. 8: Intern. J. of Cell Cloning 5, 335 (1987)
ref. 9: J. Infect. Dis. Review 5, 563 (1980), and Antiviral Res. 3, 17 (1983).

In the examples I to VII, the abbreviations used have the following meanings:
Et: ethyl
TEOC: trimethylsilylethyloxycarbonyl
TrOC: trichloroethyloxycarbonyl
Me: methyl
Boc: tert.butyloxycarbonyl
TLC: thin-layer chromatography
EtOAc: ethyl acetate
DMSO: dimethyl sulphoxide
THF: tetrahydrofuran
DME: dimethoxyethane
Bu: n-butyl
TFA: trifluoroacetic acid
DIBAL: diisobutyl aluminum hydride
MTP: 4-(4-methoxytetrahydropyranyl)

EXAMPLE I

1: $R_6$ = H, $R_7$ = CH(OMe)$_2$ :6
2: $R_6$ = H, $R_7$ = COOMe :7
3: (S)—$R_6$ = HNBoc, $R_7$ = COOMe :8
4: (R)—$R_6$ = HNBoc, $R_7$ = COOMe :9
5: (S)—$R_6$ = OMTP, $R_7$ = COOMe :10

3-S-(chloromethyl)-propionicaldehyde dimethylacetal (6)

Compound no. 1 (2.3 g, 16.9 mmol) and triethylbenzylammonium chloride (0.38 g, 1.7 mmol) are dissolved in 30 ml of bromochloromethane. KOH (1.42 g, 25 mmol) as a fine powder is added, and the mixture is stirred vigorously for 15 minutes. The solution is washed twice with distilled water and dried with brine and Na$_2$SO$_4$. After evaporation of the solvent 3.0 g (96%) of compound no. 6 is obtained (boiling point 75°–78° C. at 3.5 mm Hg; $n_D^{25}$=1.4970)

The following compounds are prepared in a similar manner:
1) 3-S-(chloromethyl)-methylpropionate (7) from (2): CIMS M/Z 184([M+Z+]), 182(M+).

2) N-[(tert.butyloxy)carbonyl]—S—[chloromethyl]-D-cysteïne methylester (8) from (3): TLC $R_f$ 0.52 (EtOAc/n-hexane, 1/1, v/v)

3) N-[(tert.butyloxy)carbonyl]—S—[chloromethyl]-L-cysteïne methylester (9) from (4): TLC see compound (8)

4) (2S)-3—S—(chloromethyl)-2—O—[4-(4'-methoxytetrahydropyranyl)]-methyl-propionate (10) from (5): TLC $R_f$=0.41 (3% MeOH in CHCl$_3$, v/v)

EXAMPLE II

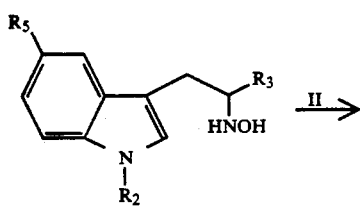

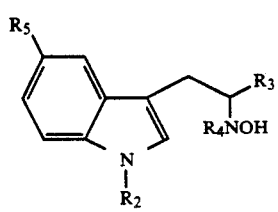

11: $R_2 = H$, $R_3 = COOEt$, $R_5 = H$
12: $R_2$, $R_3$, $R_5 = H$
13: $R_2 = Me$, $R_3 = H$, $R_5 = H$
14: $R_2 = H$, $R_3 = Me$, $R_5 = H$
15: $R_2$, $R_3 = H$, $R_5 = OMe$
16: $R_2$, $R_3 = H$, $R_5 = Br$
17a: $R_2 = H$, $R_3 = COOEt$, $R_4 = TEOC$, $R_5 = H$
17b: $R_2 = H$, $R_3 = COOEt$, $R_4 = TrOC$, $R_5 = H$
18: $R_2$, $R_3 = H$, $R_4 = TEOC$, $R_5 = H$
19: $R_2 = Me$, $R_3 = H$, $R_4 = TEOC$, $R_5 = H$
20: $R_2 = H$, $R_3 = Me$, $R_4 = TEOC$, $R_5 = H$
21: $R_2$, $R_3 = H$, $R_4 = TEOC$, $R_5 = OMe$
22: $R_2$, $R_3 = H$, $R_4 = TEOC$, $R_5 = Br$

Ethyl-α-[N,N-(2-(trimethylsilyl)ethyloxycarbonyl, hydroxy)amino]-β-indol-3-yl propanoate (17a)

1.08 g (6 mmol) of 2-trimethylsilyl)ethylchloroformate were added dropwise, while stirring, to a solution of compound 11 (1.0 g, 4 mmol) in CH$_2$Cl$_2$/dioxane, 1/1 (25 ml). The reaction was followed by TLC (elution system CHCl$_3$/MeOH, 93/7). After stirring for 2 hours, the reaction mixture was evaporated almost entirely. The residue was taken up in dichloromethane and washed with a saturated NaHCO$_3$ solution and with brine. The organic layer was dried with Na$_2$SO$_4$ and filtered off. Evaporation of the solvent provided a crystalline material which after column chromatography (CHCl$_3$/n-hexane, 99.5/0.5) provided a yield of 1.51 g (96%) of 17a. Recrystallisation from CH$_2$Cl$_2$/n-hexane: melting-point 101°–102.5° C., The following compounds were prepared in an analogous manner:

1) Ethylα-[N,N-(2,2,2-(trichloro)ethyloxycarbonyl, hydroxy) amino]-β-indol-3-yl propanoate (17b) from (11), obtained as an oil.

2) α-[N,N-(2-(trimethylsilyl)ethyloxycarbonyl, hydroxy)-amino]-β-indol-3-yl ethane (18) from (12). Recrystallisation from EtOAc/n-hexane: melting-point 95°–97° C.

3) 2-[N,N-(2-(trimethylsilyl)ethyloxycarbonyl, hydroxy)-amino]-3-(indol-3-yl)propane (19) from (13). Recrystallisation from CHCl$_3$/n-hexane: melting point 122°–125° C.

4) α-[N,N-(2-(trimethylsilyl)ethyloxycarbonyl, hydroxy)amino]-β-indol-1-methyl-3-ylethane (20) from (14) obtained as an oil.

5) α-N,N-(2-(trimethylsilyl)ethoxycarbonyl, hydroxy)-amino]-β-indol-5-methoxy-3-ylethane (21) from (15) melting point 115°–117° C.

6) α-[N,N-(2-(trimethylsilyl)ethyloxycarbonyl, hydroxy)amino]-β-indol-5-bromo-3-ylethane (22) from (16); recrystallisation from EtOAc/n-hexane; melting point 145°–148° C.

EXAMPLE III

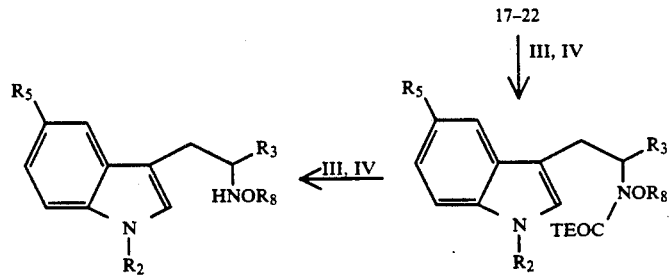

35: $R_2 = H$, $R_3$ COOEt, $R_5 = H$, $R_8 = CH_2CH_2CH_2CH(OMe)_2$ :23
36: $R_2$, $R_3$, $R_5 = H$, $R_8 = CH_2CH_2CH_2CH(OMe)_2$ :24
37: $R_2$, $R_3$, $R_5 = H$, $R_8 = CH_2CH_2CH_2COOMe$ :25
38: $R_2 = H$, $R_3 = Me$, $R_5 = H$, $R_8 = CH_2CH_2CH_2COOMe$ :26
39: $R_2$, $R_3$, $R_5 = H$, $R_8 = CH_2SCH_2CH_2CH(OMe)_2$ :27
40: $R_2$, $R_3$, $R_5 = H$, $R_8 = CH_2SCH_2CH_2COOMe$ :28
41: $R_2$, $R_3$, $R_5 = H$, (S)—$R_8 = CH_2SCH_2CH(NHBoc)COOMe$ :29
42: $R_2 = Me$, $R_3$, $R_5 = H$, (S)—$R_8 = CH_2SCH_2CH(NHBoc)COOMe$ :30
43: $R_2$, $R_3 = H$, $R_5 = OMe$, (s)—$R_8 = CH_2SCH_2CH(NHBoc)COOMe$ :31
44: $R_2$, $R_3 = H$, $R_5 = Br$, (S)—$R_8 = CH_2SCH_2CH(NHBoc)COOMe$ :32
45: $R_2$, $R_3$, $R_5 = H$, (R)—$R_8 = CH_2SCH_2CH(NHBoc)COOMe$ :33
46: $R_2$, $R_3$, $R_5 = H$, (S)—$R_8 = CH_2SCH_2CH(OMTP)COOMe$ :34

Ethyl α-(1,1-dimethoxy-4-butyloxyamino-β-(indol-3-yl) propanoate (35)

A solution of 17a (1568 mg, 4 mmol), 4-bromo-1,1-dimethoxybutane (1575 mg, 8 mmol) and K$_2$CO$_3$ (828 mg, 6 mmol) in DMSO (25 ml) was stirred at 45° C. for 24 hours. The reaction mixture was diluted with dichloromethane (100 ml), after which the greater part of the DMSO was removed by washing with water and 0.1N HCl. The organic layer was washed with brine and dried with $Na_2SO_4$. Evaporation of the reaction mixture provided an oil which after column chromatography ($CHCl_3$/n-hexane 90/10) provided a yield of 1.37 g (67%) of compound 23. A solution of 23 (1.35 9, 2.65 mmol) and tetrabutylammoniumfluoride (5.3 ml 1N solution in THF) in THF (25 ml) was stirred for 2 hours, after which the reaction mixture was washed successively with a saturated $NaHCO_3$ solution and with brine, and dried with $MgSO_4$. Evaporation of the solvent provided a crude mixture of 35 which after purification by means of column chromatography ($CHCl_3$) provided 706 mg (78%) of 35 as an oil.

EXAMPLE IV

α-(1,1-dimethoxy-4-butyloxamino)-β-(indol-3-yl)ethane (36)

Sodium hydride (41 mg, 1.7 mmol) was added while stirring to a cooled (−10° C.) solution of 18 (500 mg, 1.56 mmol) in dry DME (10 ml) under an atmosphere of argon. During warming up to room temperature $H_2$-formation was observed. The formed bright solution was added dropwise, while stirring, to a solution of 4-bromo-1,1-dimethoxybutane (368 mg, 1.87 mmol) and NaI (260 mg, 1.87 mmol) in DME (10 ml). After stirring the reaction mixture for 24 hours at room temperature, it was washed successively with a 0.1N HCl solution and with brine, and was dried with $MgSO_4$. Evaporation of the solvent provided crude 24 which was added to a solution of $Bu_4NF$ (2 eq.) in THF. After stirring for 2 hours the reaction was completed. The reaction mixture was washed successively with a saturated $NaHCO_3$ solution and with brine, and was dried with $MgSO_4$. Evaporation of the solvent provided a crude mixture of compound 36 which after purification by means of column chromatography ($CHCl_3$/MeOH, 99/1) provided 306 mg (67%) of 36 as an oil.

The following compounds were prepared in an analogous manner:

1) α-methyl-4-butanoate oxamino)-β-(indol-3-yl)ethane (37) via (25); as an oil.
2) 2-(methyl-4-butanoate oxamino)-3-(indol-3-yl)propane (38) via (26); as an oil.
3) Compound 39 via (27); was obtained as an oil.
4) Compound 40 via (28); was obtained as an oil.
5) (D)-compound 41 via (29), oil; $[\alpha]_D^{20} = +5°$ (c=0.5; methanol).
6) D-compound 42 via (30); oil
7) D-compound 43 via (31); oil $[\alpha]_D^{22} = +16.7°$ (c=3.6, methanol)
8) D-compound 44 via (32); oil
9) (L)-compound 45 via (33); oil; $[\alpha]_D^{20} = -5°$ (c=3; methanol).
10) D-compound 46 via (34); oil, $[\alpha]_D^{22} = +17.5°$ (c=3.25, methanol).

EXAMPLE V

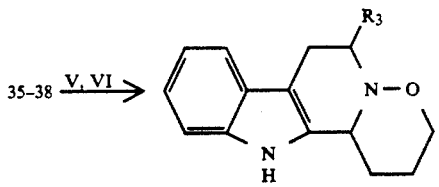

35–38 $\xrightarrow{V, VI}$ 47a, 47b: $R_3$ = COOEt
48: $R_3$ = H
49a, 49b: $R_3$ = $CH_3$

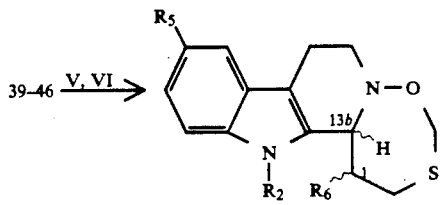

39–46 $\xrightarrow{V, VI}$

50: $R_2$, $R_5$, $R_6$ = H
51: $R_2$, $R_5$ = H, (1S, 13bS)$R_6$ = HNBoc
52: $R_2$, $R_5$ = H, (1S, 13bR)$R_6$ = HNBoc
53: $R_2$ = Me, $R_5$ = H, (1S, 13bS)$R_6$ = HNBoc
54: $R_2$ = Me, $R_5$ = H, (1S, 13bSR)$R_6$ = HNBoc
55: $R_2$ = H, $R_5$ = OMe, (1S, 13bS)$R_6$ = HNBoc
56: $R_2$ = H, $R_5$ = OMe, (1S, 13bR)$R_6$ = HNBoc
57: $R_2$ = H, $R_5$ = Br, (1S, 13bS)$R_6$ = HNBoc
58: $R_2$ = H, $R_5$ = Br, (1S, 13bR)$R_6$ = HNBoc
59: $R_2$, $R_5$ = H, (1R, 13bR)$R_6$ = HNBoc
60: $R_2$, $R_5$ = H, (1R, 13bS)$R_6$ = HNBoc
61: $R_2$, $R_5$ = H, (1S, 13bR)$R_6$ = OMTP
62: $R_2$, $R_5$ = H, (1S, 13bR)$R_6$ = OH

Cyclisation of dimethoxy acetals under acidic conditions

Cis-6-ethoxycarbonyl-octahydrooxazino[2,3-a]-β-carboline (47a) and trans-6-ethoxycarbonyloctahydrooxazino-β-carboline (47b)

A solution of 35 (650 mg, 1.79 mmol), TFA (228 mg, 2 mmol) in dichloromethane (20 ml) was stirred at room temperature for 4 hours. The reaction mixture was washed successively with a 0.1N solution of $NaHCO_3$ and with brine, and was dried with $Na_2SO_4$. After evaporating the solvent the crystalline material was purified by means of column chromatography (n-hexane/EtOAc, 75/25), providing 415 mg (77%) of 47a and 110 mg (20%) of 47b.

Compound 47a: Crystallisation from EtOAc/n-hexane; melting-point 156°–158° C.

Compound 47b: Crystalline from EtOAc/n-hexane; melting-point 145°–147° C.

In an analogous manner were prepared:
1) Octahydrooxazino[2.3-a]-β-carboline (48), melting-point 178°–180° C.
2) (±)-Deamino, debromo Eudistomin L (50), melting-point 158°–160° C.

EXAMPLE VI

Reductive Ring Closure

Compound 48

DIBAL (1N, 3 ml) in toluene was added dropwise, while stirring, to a cooled (−70° C.) solution of compound 37 (390 mg, 1.4 mmol) in dry toluene (75 ml)

under an atmosphere of argon. After stirring for 2 hours the excess of DIBAL was destroyed at −70° C. by carefully adding dropwise TFA (5 eq.) in toluene, after which the reaction mixture was poured in ice-water (100 ml). The organic layer was separated and the neutralised aqueous layer was washed twice with 100 ml of EtOAc. The combined organic layer was washed with a brine solution and dried with MgSO$_4$. Evaporation of the solvent provided crystalline 48, which was purified by means of column chromatography (CHCl$_3$/MeOH, 99/1). Yield 241 mg (76%) of 48, melting-point 178°–180° C.

In an analogous manner were prepared:
1) Cis-6-methyl-octahydrooxazino[2,3-a]-β-carboline (49a), melting-point 194°–196° C. and trans-6-methyl-octahydrooxazino[2,3-a]-β-carboline (49b), melting-point 174°–176° C.
2) (±)-Deamino, debromo Eudistommin L (50), melting-point 158°–160° C.
3) (1S,13bS)-debromo-14-tert.butyloxyxcarbonyl Eudistomin L (51), melting-point 214°–216° C., $[\alpha]_D^{25} = -60°$ and (1S,13bR)-debromo-14-tert.butyloxycarbonyl Eudistomin L (52), $[\alpha]_D^{25} = -3°$.
4) (1S,13bS)-debromo-13-methyl-14-tert.butyloxycarbonyl Eudistomin L (53), $[\alpha]_D^{22} = -152.2°$ (c=2.05 in methanol)
5) (1S,13bR)-debromo-13-methyl-14-tert.butyloxycarbonyl Eudistomin L (54), $[\alpha]_D^{22} = +90.2$ (c=2.35 in methanol)
6) (1S,13bS)-5-methoxy-14-tert.butyloxycarbonyl Eudistomin L (55), $[\alpha]_D^{22} = -55.3°$ (c=4.05 in methanol)
7) (1S,13bR)-5-methoxy-14-tert.butyloxycarbonyl Eudistomin L (56), $[\alpha]_D^{22} = -23.1°$ (c=5.10 in methanol)
8) (1S,13bS)-14-tert.butyloxycarbonyl Eudistomin L, (57), $[\alpha]_D^{22} = -43.8°$ (c=0.8 in methanol)
9) (1S,13bR)-14-tert.butyloxycarbonyl Eudistomin L, (58), $[\alpha]_D^{22} = -40.6°$ (c=0.96 in methanol)
10) (1R,3bR)-debromo-14-tert.butyloxycarbonyl Eudistomin L (59), melting point 213°–216° C., $[\alpha]_D^{25} = +61°$, and (1R,13bS)-debromo-14-tert.butyloxycarbonyl Eudistomin L (60), solid material, not crystallisable; $[\alpha]_D^{25} = +4°$.
11) (1S,13bR)-debromo-1-[4-(4'-methoxytetrahydropyranyl)] Eudistomin L, (61), $[\alpha]_D^{22} = +41.8°$ (c=1.7, methanol)
12) (1S,13bR)-debromo-1-hydroxy Eudistomin L, (62), $[\alpha]_D^{22} = -3.6°$ (c=2.2, methanol)

EXAMPLE VII

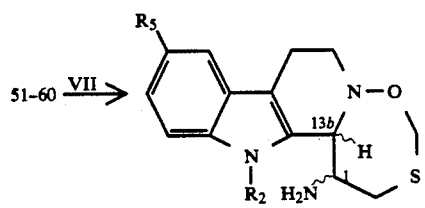

-continued
63: R$_2$, R$_5$ = H, (1S, 13bR)
64: R$_2$, R$_5$ = H, (1S, 13bR)
65: R$_2$ = Me, R$_5$ = H, (1S, 13bS)
66: R$_2$ = Me, R$_5$ = H, (1S, 13bR)
67: R$_2$ = H, R$_5$ = OMe, (1S, 13bS)
68: R$_2$ = H, R$_5$ = OMe, (1S, 13bR)
69: R$_2$ = H, R$_5$ = Br, (1S, 13bS)
70: R$_2$ = H, R$_5$ = Br, (1S, 13bR)
71: R$_2$, R$_5$ = H, (1R, 13bR)
72: R$_2$, R$_5$ = H, (1R, 13bS)

Removal of protective Boc-group by means of trimethylsilyl iodide;

(1S,13bS)-debromo Eudistomin L (63)

Compound 51 (327 mg, 0.87 mmol) is dissolved in 100 ml of acetonitrile. Trimethylsilyl chloride (190 mg, 1.74 mmol) and NaI (260 mg, 1.74 mmol) are added, and the mixture is stirred for 3 hours. The residue obtained after removal of the solvent under reduced pressure is taken up in CH$_2$Cl$_2$ and washed with water and with brine. The organic layer is dried with MgSO$_4$ and evaporated. The residue is purified by means of column chromatography (EtOAc/n-hexane, 1/1), and 225 mg (94%) of compound 63 is obtained; $[\alpha]_D^{22} = -115.3$ (c=3.0, methanol).

In a similar manner the following compounds have been prepared:
1) (1S,13bR)-debromo Eudistomin L, (64), $[\alpha]_D^{22} = +23.2$ (c=3.8, methanol)
2) (1S,13bS)-debromo-13-methyl Eudistomin L, (65)
3) (1S,13bR)-debromo-13-methyl Eudistomin L, (66)
4) (1S,13bS)-5-methoxy Eudistomin L, (67), $[\alpha]_D^{22} = -76.6$ (c=2.7, methanol)
5) (1S,13bR)-5-methoxy Eudistomin L, (68), $[\alpha]_D^{22} = +3.0$ (c=2.0, methanol)
6) (1S,13bS) Eudistomin L, (69), $[\alpha]_D^{22} = -64.5$ (c=2.9, methanol)
7) (1S,13bR) Eudistomin L, (70)
8) (1R,13bR)-debromo Eudistomin L, (71), $[\alpha]_D^{22} = +111.4°$ (c=2.1, methanol)
9) (1R,13bS)-debromo Eudistomin L, (72) $[\alpha]_D^{22} = -28.8$ (c=1.7, methanol)

EXAMPLE VIII

The antitumour activity of some eudistomin derivatives and the reference antitumour drug was assessed in an in-vitro test with high predictive power for in-vivo activity. In this assay the inhibition of P 388 leukemia cells colony formation was determined at several concentrations of the test compounds as described in reference 8. The activity is expressed as an ID$_{50}$ value, which indicates the dose causing 50% inhibition with respect to untreated control cells. The following data were found:

TABLE A

| Antitumor activity of eudistomin derivatives in P 388 leukemia cells. | |
| --- | --- |
| compound | ID$_{50}$ (mg/ml) |
| 50 | no activity at 1.0 |
| 63 | 0.042 |
| 67 | 0.0038 |
| adriamycin | 0.020 |

EXAMPLE IX

Antiviral activity of some eudistomin derivatives was determined in a large number of in-vitro assays as described in reference 9. These tests are all based on the inhibition of virus induced cytopathogenicity. Depending upon the virus studied, different cell cultures were used. As a general rule it is accepted that a compound is considered as antivirally active when the minimal inhibition concentration (MIC-value) is at least ten-fold lower than the minimal cytotoxic concentration (MCC-value). The results for compounds 50, 63 en 67 together with ribavirin as a standard are given in the Tables B–E. For both compound 63 and especially 67 an exceptionally wide range of activities in the 22 antiviral assays is found. New compound 67 has the additional advantage of a 10-fold higher potency as compared with known compound 63.

TABLE B

Cytotoxic and Antiviral Activity of eudistomin derivatives in MDCK cell cultures.

| Compound | MCC µg/ml | MIC (µg/ml) influenza virus A (Ishikawa) | MIC (µg/ml) influenza virus B (Singapore) |
|---|---|---|---|
| 63 | 8 | 0.8 | 0.8 |
| 50 | 80 | >40 | >40 |
| 67 | 0.8 | >0.32 | >0.32 |
| Ribavirin | >200 | 15 | 15 |

TABLE C

Cytotoxic and Antiviral Activity of eudistomin derivatives in Hela cell cultures.

| Compound | MCC (µg/ml) | Respiratory syncytial virus (Lung) | Vesicular stomatitis virus | Coxsackie virus B4 | Polio virus |
|---|---|---|---|---|---|
| 63 | ≧4 | 0.8 | 0.2 | 0.55 | 0.7 |
| 50 | ≧30 | >8 | >10 | >10 | >10 |
| 67 | 2 | 0.15 | 0.03 | 0.045 | 0.045 |
| Ribavirin | ≧400 | 3 | 20 | 70 | 110 |

TABLE D

Cytotoxic and Antiviral Activity of eudistomin derivatives in Vero cell cultures.

| Compound | MCC (µg/ml) | parainfluenza-3 virus | Reovirus-1 | Sindbis virus | Coxsasckie virus B4 | Semliki forest virus |
|---|---|---|---|---|---|---|
| 63 | ≧4 | >0.6 | 0.4 | 0.35 | 0.55 | 0.45 |
| 50 | ≧40 | >10 | >10 | >10 | >25 | >25 |
| 67 | ≧1 | 0.55 | 0.045 | 0.045 | 0.07 | 0.11 |
| Ribavirin | >400 | 135 | 125 | >235 | >300 | >300 |

TABLE E

Cytotoxic and Antiviral Activity of eudistomin derivates in primary rabbit kidney (PRK) cell cultures

| Compound | MCC (µg/ml) | Herpes simplex virus-1 (KOS) | Herpes simplex virus-1 (F) | Herpes simplex virus-1 (McInyre) | Herpes simplex virus-2 (G) | Herpes simplex virus-2 (196) | Herpes simplex virus-2 (Lyons) | Vaccinia virus | Vesicular stomatitis virus | Herpes simplex virus-1 (B2006) C158/77 | Herpes simplex virus-1 (B2006) C137/101 | Herpes simplex virus-1 (B2006) #3 |
|---|---|---|---|---|---|---|---|---|---|---|---|---|
| 63 | ≧25 | 1.35 | 0.25 | 0.2 | 0.2 | 0.2 | 0.38 | 0.25 | 0.2 | 0.7 | 0.7 | 0.85 |
| 50 | ≧120 | >70 | >70 | >70 | >120 | >70 | >70 | >70 | >70 | >70 | >70 | >70 |
| 67 | ≧2.5 | 0.045 | 0.039 | 0.013 | 0.012 | 0.014 | 0.023 | 0.012 | 0.015 | 0.023 | 0.0085 | 0.055 |
| Ribavirin | ≧400 | >200 | >200 | >200 | >200 | >200 | >200 | 30 | >400 | >200 | >200 | >200 |

We claim:

1. A method of preparing an N-oxo-tetrahydro-β-carboline of formula 1:

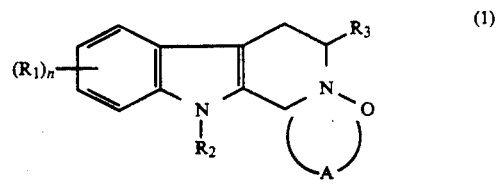

wherein $R_1$ is lower alkyl, lower alkoxy, halogen, trifluoromethyl, lower alkylthio, hydroxy, amino, or mono- or dialkyl- or acylamino having 1–4 carbon atoms, wherein the acyl group is derived from carboxylic acid only;

n has the value 0, 1 or 2;

$R_2$ is hydrogen, lower alkyl or acyl having 1–4 carbon atoms, said acyl being derived from carboxylic acid only;

$R_3$ is hydrogen, lower alkyl, alkoxycarbonyl having 1–4 carbon atoms or phenyl which is unsubstituted or substituted by a group $R_1$; and A is —$(CH_2)_p$—Y—$CH_2$ which is unsubstituted or substituted by one or more of the substituents: alkyl having 1–4 carbon atoms, alkoxycarbonyl having 1–4 carbon atoms, alkanoyl having 1–4 carbon atoms, alkoxy having 1–4 carbon atoms, hydroxy, oxo, amino, mono- or dialkylamino having 1–4 carbon atoms, or alkanoyl- or alkoxycarbonylamino having 1–4 carbon atoms, wherein p is 1–3, —Y—CH$_2$— is connected to the —O— present in the compound of formula 1, and Y is O, S or N;

comprising intramolecular ring closing a compound of formula 2

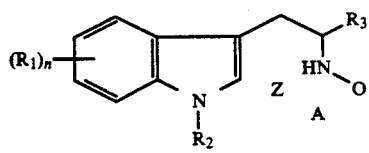

wherein R$_1$, n, R$_2$, R$_3$ and A are as defined above and Z is a group which is capable of performing a double electrophilic attack on both the aliphatic nitrogen atom and the carbon atom of the indole ring, said group being selected from an aldehyde function, an acetal function, an ester function and a group which can be converted to such a function during the ring closure reaction.

2. A method as claimed in claim 1, wherein Z is selected from an aldehyde function, an acetal function and a group which can be converted into such a function during the ring closure reaction.

3. A method as claimed in claim 1 or 2, wherein Z is a dimethylacetal function.

4. A method as claimed in claim 3, wherein the reaction is carried out in the presence of an acid catalyst.

5. A method as claimed in claim 3, wherein Z is an alkoxycarbonyl group.

6. A method as claimed in claim 5, wherein the reaction is carried out in the presence of a reductor.

7. A method as claimed in claim 1, wherein the production of the compound of formula (2) comprises
selectively protecting the aliphatic nitrogen atom of a compound of formula (3)

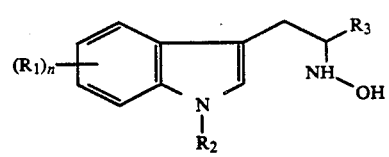

wherein R$_1$, n, R$_2$ and R$_3$ are defined as in claim 1;
converting the protected compound with a compound of formula

wherein Z and A are defined as in claim 1 and X is a leaving group selected from the group consisting of halogen and sulphonate, into a protected compound of formula (2); and
disprotecting the resulting compound of formula (2).

8. A method as claimed in claim 7, wherein X is halogen or sulphonate.

9. An N-oxo-tetrahydro-β-carboline of formula 1:

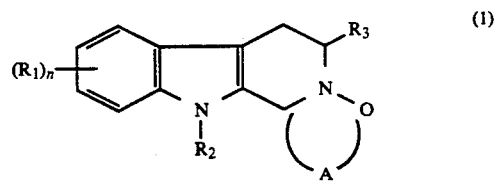

wherein
R$_1$ is lower alkyl, lower alkoxy, halogen, trifluoromethyl, lower alkylthio, hydroxy, amino, or mono- or dialkyl- or acylamino having 1–4 carbon atoms, wherein the acyl group is derived from carboxylic acid only;
n has the value 0, 1 or 2;
R$_2$ is hydrogen, lower alkyl or acyl having 1–4 carbon atoms, the acyl being derived from carboxylic acid only;
R$_3$ is hydrogen, lower alkyl, alkoxycarbonyl having 1–4 carbon atoms or phenyl which is unsubstituted or substituted by a group R$_1$, and
A is —(CH$_2$)$_p$—Y—CH$_2$ which is unsubstituted or substituted by one or more of the substituents: alkyl having 1–4 carbon atoms, alkoxycarbonyl having 1–4 carbon atoms, alkanoyl having 1–4 carbon atoms, alkoxy having 1–4 carbon atoms, hydroxy, oxo, amino, mono- or dialkylamino having 1–4 carbon atoms, or alkanoyl- or alkoxycarbonylamino having 1–4 carbon atoms, wherein p is 1–3, —Y—CH$_2$— is connected to the —O— present in the compound of formula 1, and Y is O, S or N;
or a therapeutically acceptable salt thereof;
with the exception of compounds of formula (5)

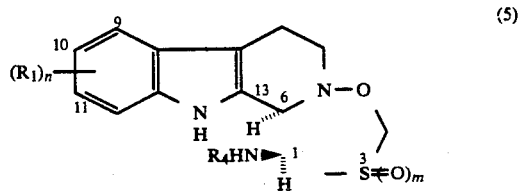

wherein
a) m and n are 0, and R$_4$ is hydrogen or tert.butoxycarbonyl (Boc);
b) n is 1, m is 0 or 1, R$_1$ is 11—Br, and R$_4$ is hydrogen or acetyl;
c) n is 1, m is 0, R$_1$ is 10—Br, and R$_4$ is hydrogen or Boc;
d) n is 2, m is 0, R$_1$ is 10—OH or 11—Br, and R$_4$ is hydrogen; or
e) n is 2, m is 0, R$_1$ is 9—Br or 10—OH and R$_4$ is hydrogen; with the proviso that the stereochemical configuration at each of C$_1$ and C$_{13b}$ is the S-configuration, and that the optionally oxide substituent at S$_3$ is in the cis position relative to the substituent at C$_1$.

10. A method of preparing a Eudistomin derivative of formula

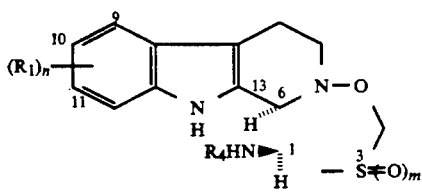

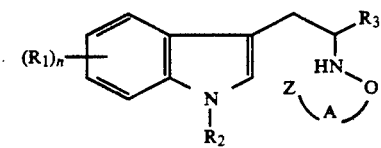

wherein

R₁ is lower alkyl, lower alkoxy, halogen, trifluoromethyl, lower alkylthio, hydroxy, amino or mono- or dialkyl- or acylamino having 1-4 carbon atoms, wherein the acyl group is derived from carboxylic acid only;

n has the value 0, 1 or 2;

R₄ is hydrogen; and m has the value 0 or 1; comprising treating a compound of formula (5) wherein R₄ is tert.butyloxycarbonyl with a trimethylsilyl halide.

11. A pharmaceutical composition comprising a pharmaceutically effective amount of a compound as claimed in claim 9 as an active substance and a pharmaceutically acceptable carrier.

12. A composition as claimed in claim 11, comprising (1S, 13bS)-5-methoxy Eudistomin L as an antitumorally effective compound and a broad spectrum antivirally effective component.

13. An intermediate compound of formula (2)

wherein

R₁ is lower alkyl, lower alkoxy, halogen, trifluoromethyl, lower alkylthio, hydroxy, amino, or mono- or dialkyl- or acylamino having 1-4 carbon atoms, wherein the acyl group is derived from carboxylic acid only;

n has the value 0, 1 or 2;

R₂ is hydrogen, lower alkyl or acyl having 1-4 carbon atoms, the acyl being derived from carboxylic acid only;

R₃ is hydrogen, lower alkyl, alkoxycarbonyl having 1-4 carbon atoms or phenyl which is unsubstituted or substituted by a group R₁;

A is —(CH₂)ₚ—Y—CH₂ which is unsubstituted or substituted by one or more of the substituents: alkyl having 1-4 carbon atoms, alkoxycarbonyl having 1-4 carbon atoms, alkanoyl having 1-4 carbon atoms, alkoxy having 1-4 carbon atoms, hydroxy, oxo, amino, mono- or dialkylamino having 1-4 carbon atoms, or alkanoyl- or alkoxycarbonylamino having 1-4 carbon atoms, wherein p is 1-3, —Y—CH₂— is connected to the —O— present in the compound of formula (1), and Y is O, S or N; and Z is an aldehyde function, an acetal function or a group which can be converted into such a function.

14. A method as claimed in claim 4, wherein the acid catalyst is trifluoroacetic acid.

15. A method as claimed in claim 5, wherein the reductor is diisobutyl aluminum hydride.

* * * * *

UNITED STATES PATENT AND TRADEMARK OFFICE
CERTIFICATE OF CORRECTION

PATENT NO. : 5,106,840

DATED : April 21, 1992

INVENTOR(S) : Peter H. H. HERMKENS et al.

It is certified that error appears in the above-identified patent and that said Letters Patent is hereby corrected as shown below:

Column 16, line 37 (claim 15, line 1), "5" should be --6--.

Columns 3, 14 and 15, formula (5) should read as follows:

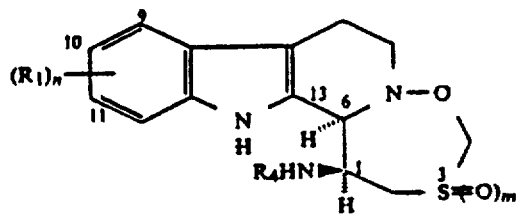

(5)

Signed and Sealed this

Nineteenth Day of April, 1994

*Attest:*

BRUCE LEHMAN

*Attesting Officer*   *Commissioner of Patents and Trademarks*